United States Patent [19]
Webster, Jr.

[11] Patent Number: 5,782,239
[45] Date of Patent: Jul. 21, 1998

[54] UNIQUE ELECTRODE CONFIGURATIONS FOR CARDIOVASCULAR ELECTRODE CATHETER WITH BUILT-IN DEFLECTION METHOD AND CENTRAL PULLER WIRE

[75] Inventor: Wilton W. Webster, Jr., Altadena, Calif.

[73] Assignee: Cordis Webster, Inc., Baldwin Park, Calif.

[21] Appl. No.: 488,107

[22] Filed: Jun. 7, 1995

Related U.S. Application Data

[63] Continuation-in-part of Ser. No. 432,011, May 1, 1995, Pat. No. 5,628,313, which is a continuation-in-part of Ser. No. 906,546, Jun. 30, 1992, Pat. No. 5,411,025.

[51] Int. Cl.⁶ .................................................. A61B 5/0402
[52] U.S. Cl. .................................. 128/642; 607/122
[58] Field of Search ........................... 128/642; 607/122, 607/126

[56] References Cited

U.S. PATENT DOCUMENTS

| | | | |
|---|---|---|---|
| Re. 34,502 | 1/1994 | Webster, Jr. | 607/125 |
| 3,664,347 | 5/1972 | Harmjanz | 128/404 |
| 3,890,977 | 6/1975 | Wilson | 128/418 |
| 4,522,212 | 6/1985 | Gelinas et al. | 128/642 |
| 4,531,943 | 7/1985 | Van Tassel et al. | 604/280 |
| 4,699,147 | 10/1987 | Chilson et al. | 128/642 |
| 4,960,134 | 10/1990 | Webster, Jr. | 128/786 |
| 5,010,894 | 4/1991 | Edhag | 128/785 |
| 5,045,072 | 9/1991 | Castillo et al. | 604/280 |
| 5,156,151 | 10/1992 | Imran | 128/642 |
| 5,311,866 | 5/1994 | Kagan et al. | 128/642 |
| 5,324,284 | 6/1994 | Imran | 606/15 |
| 5,449,381 | 9/1995 | Imran | 607/122 |
| 5,549,661 | 8/1996 | Kordis et al. | 128/642 |
| 5,551,426 | 9/1996 | Hummel et al. | 128/642 |

FOREIGN PATENT DOCUMENTS

| | | |
|---|---|---|
| 0009732 | 4/1980 | European Pat. Off. |
| 2659240 | 9/1991 | France |
| 4025369 | 2/1991 | Germany |
| 8906148 | 7/1989 | WIPO |

*Primary Examiner*—Lee S. Cohen
*Attorney, Agent, or Firm*—Christie, Parker & Hale, LLP

[57] ABSTRACT

An electrophysiological mapping device includes an outer catheter, an inner catheter slidable within the outer catheter, and an electronic activation and recording device for electrically activating electrodes on the inner catheter and/or recording electric signals received by the electrodes. The distal end of the inner catheter comprises a plurality of arms that carry electrodes. The arms bow outwardly upon extension of the inner catheter from the outer catheter to form a three-dimensional shape. Each arm has a spine of a superelastic material. Each spine is semicircular in section, and is disposed within a portion of a flexible sheath, the electrode lead wires being disposed in the rest of the sheath. The electrodes are formed from the ends of the insulated electrode lead wires which pass through the sheath, are wrapped around the sheath and then stripped of their insulation. The proximal and distal ends of the spines are fixed to proximal and distal fittings, each having a polygonal segment having flat sides which engage the flat surfaces of the spines and a clamping ring to secure the spines to the segments. A puller wire is attached to the distal end of the three-dimensional shape and passes through the inner catheter to the proximal end of the catheter where it is connected to a deflectable control handle which applies a proximally directed force to the puller wire causing the three-dimensional shape to expand outwardly. The puller wire is coated with TEFLON inside the inner catheter and with polyurethane outside the catheter allowing the inner catheter to translate smoothly inside the inner catheter and to be sealed at its distal end against the flow of blood. Multiple electrode configurations are provided to meet specific ablation and mapping requirements.

7 Claims, 10 Drawing Sheets

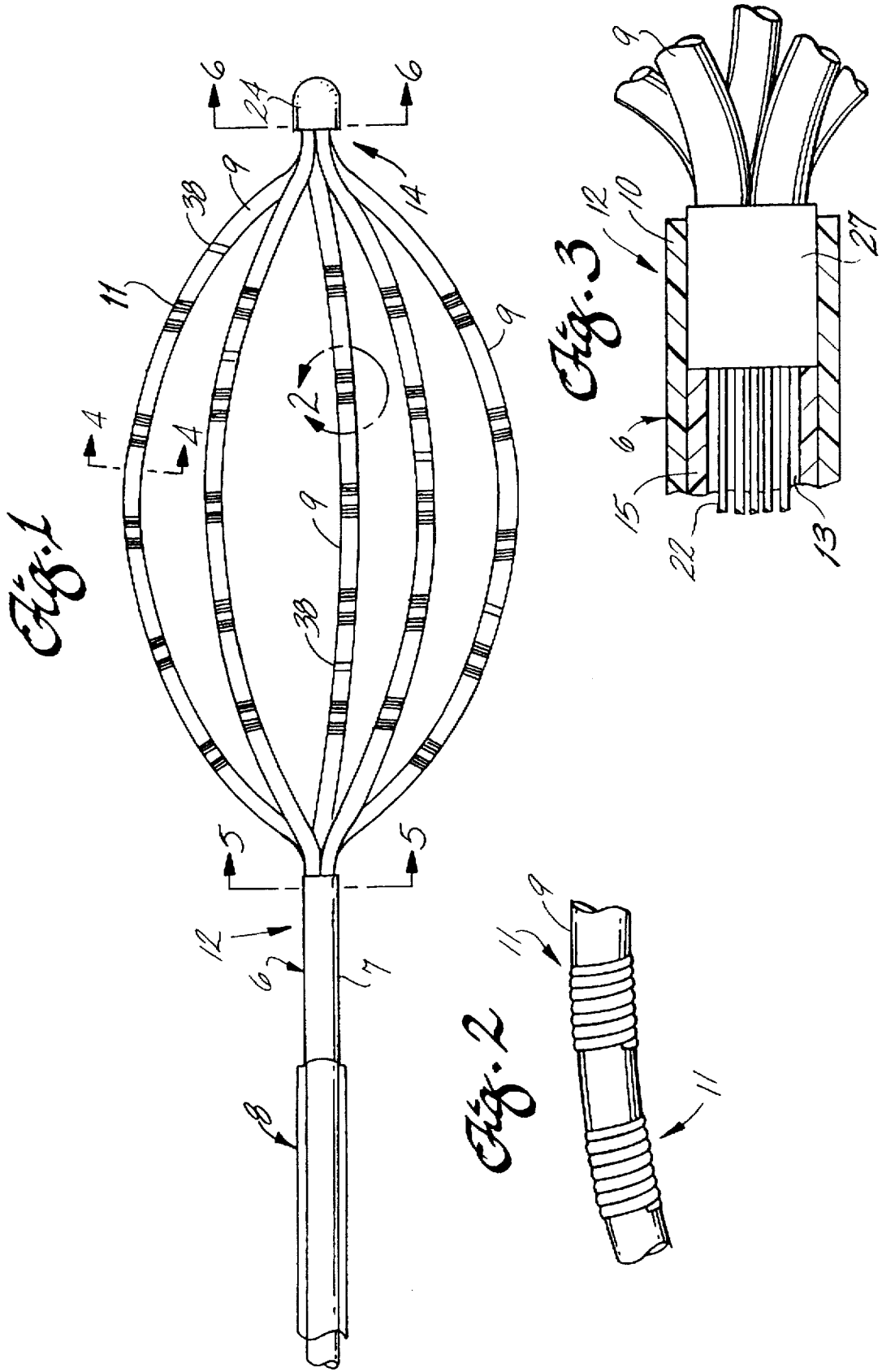

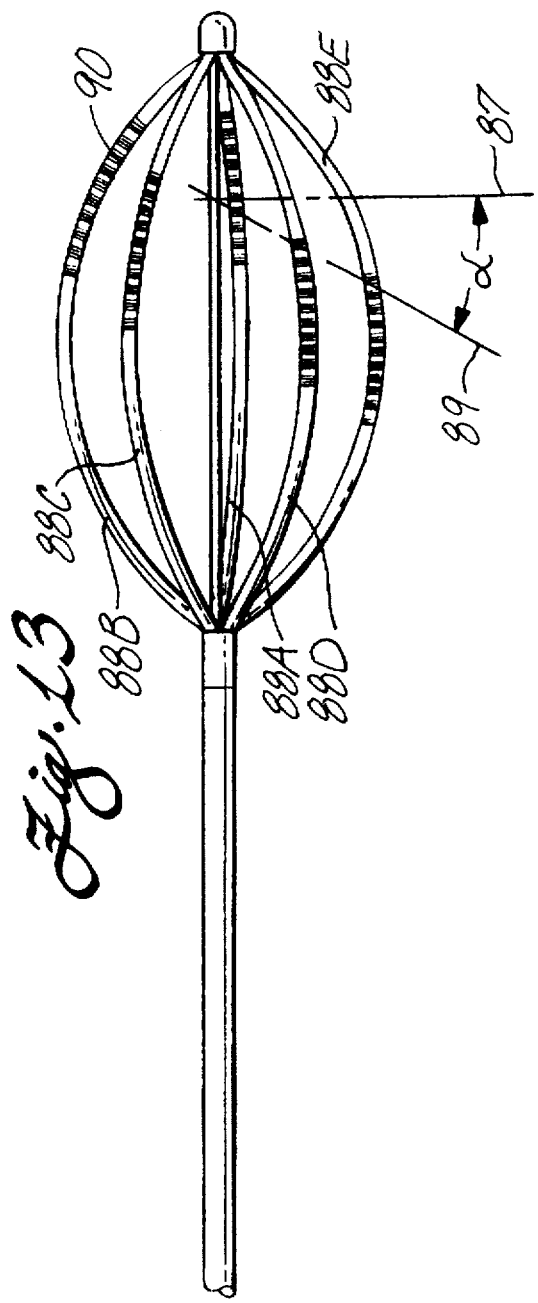
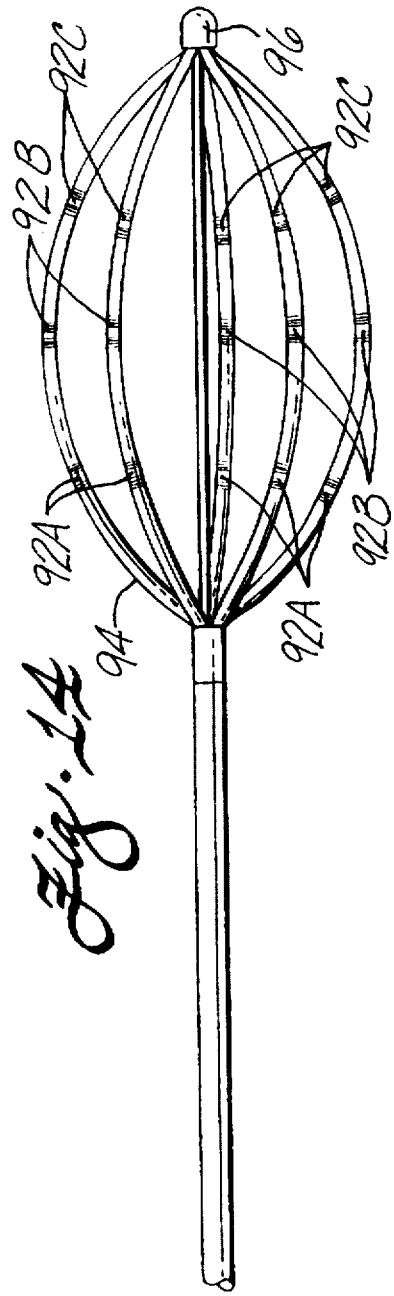

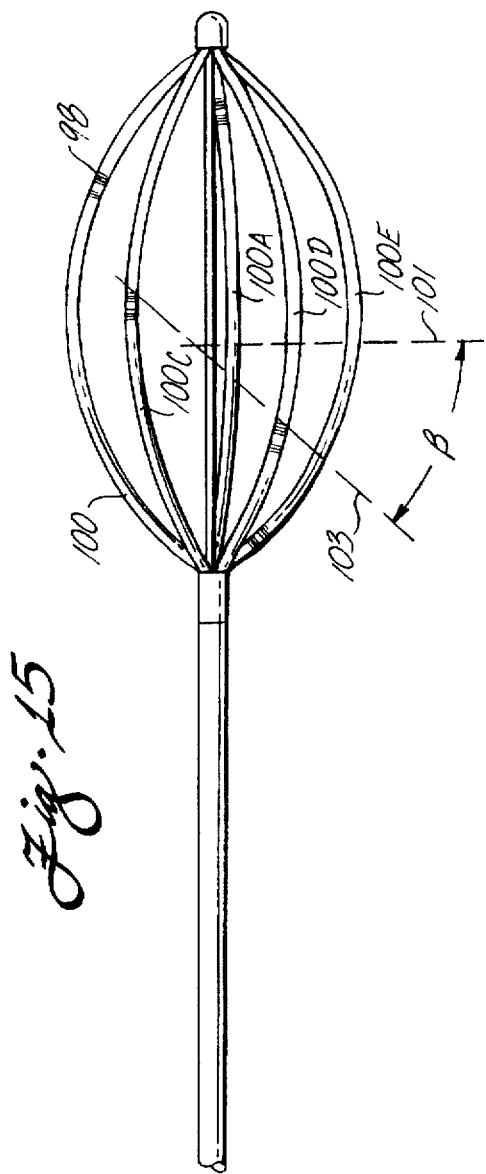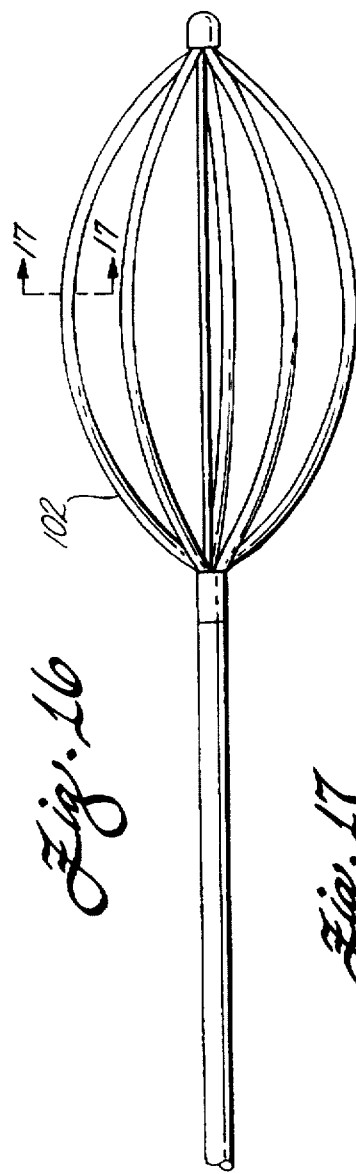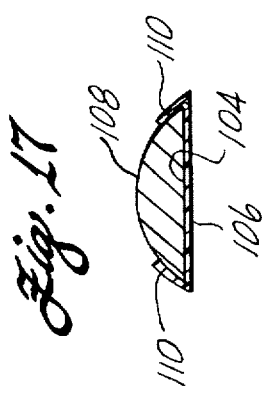

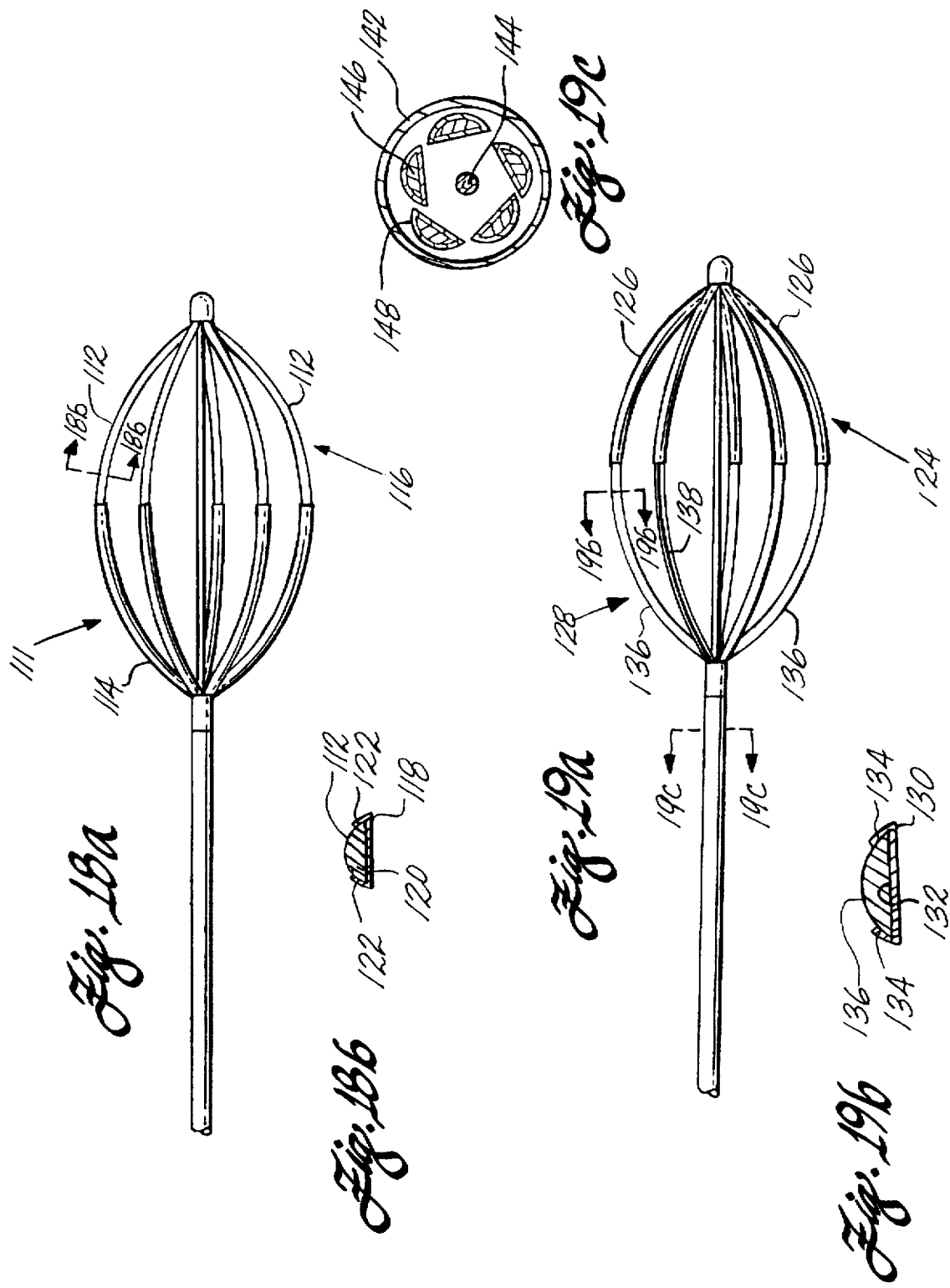

UNIQUE ELECTRODE CONFIGURATIONS FOR CARDIOVASCULAR ELECTRODE CATHETER WITH BUILT-IN DEFLECTION METHOD AND CENTRAL PULLER WIRE

RELATED APPLICATION

This application is a continuation-in-part of U.S. patent application Ser. No. 08/432,011 filed on May 1, 1995, now U.S. Pat. No. 5,628,313 which is a continuation-in-part of U.S. patent application Ser. No. 07/906,546, filed Jun. 30, 1992 now U.S. Pat. No. 5,411,025 which are incorporated herein by reference.

FIELD OF THE INVENTION

The present invention relates to cardiovascular catheters and, in particular, to such catheters having a retractable basket-shaped electrode array formed by a plurality of arms, each arm supporting a plurality of spaced-apart electrodes.

BACKGROUND OF THE INVENTION

Electrophysiology is a specialty within the field of cardiology for diagnosis and treatment of electrical abnormalities of the heart. Diagnosis is performed using electrode-bearing catheters placed within the heart chambers. Electrodes are positioned along a catheter shaft in a primarily two-dimensional array, although electrode elements spaced laterally around the catheter shaft give the array a very limited third dimension. Understandably, this third dimension is limited because of the small catheter shaft diameter required for such catheters as they are introduced into the heart via the veins and arteries of the body.

Electrical abnormalities are typically diagnosed by detecting the course of electrical activation paths along the endocardial surfaces of the heart chambers over time. To do this, the cardiologist may place several catheters within one or more chambers of the heart to get a better "picture" of this electrical activity. Sometimes this electrical activity is cyclical, i.e., repeats fairly well from heartbeat to heartbeat. In such cases, one catheter may serve to perform the diagnosis by moving the electrodes to various regions and then point-by-point comparing activation times with a reference. This reference may be the external EKG or another electrode catheter maintained in a stable position within a heart chamber.

However, certain types of electrical activity within a heart chamber are not cyclical. Examples include arterial flutter or arterial fibrillation, and ventricular tachycardia originating in scars in the wall of the ventricle that have resulted from infarcts. Such electrical activity is random from beat to beat. To analyze or "map" this type of electrical activity, the "picture" must be obtained during one beat. In other words, all the points of the map or picture must be obtained simultaneously within one-tenth of a second.

One solution to improve mapping is disclosed in U.S. Pat. Nos. 4,522,212 to Gelinas et al. and 4,699,147 to Chilson et al. which are incorporated herein by reference. In these patents, a catheter has, at its distal end, multiple lead-carrying arms which extend in a three-dimensional array, each arm having an inner central rib and electrodes spaced along its length. In Chilson et al., the arms are fixed at their distal end, but free to move within an outer catheter tube at their proximal end. The lead-carrying arms may be retracted into and extended from the outer catheter tube. The distal end of the catheter is directed to the designated areas of the heart and withdrawn, with the lead-carrying arms retracted within the outer catheter tube. Once at the designated areas, the arms are extended from the outer catheter tube to form a three-dimensional shape, referred to as an "elliptical envelope."

The catheter described in Chilson et al. is able to hold a large number of electrodes in different relative positions within a heart chamber. By this means, the cardiologist can obtain a map of electrical activity in one heartbeat by recording electrical signals from all the electrodes simultaneously. This is done by analyzing the spatial and temporal relationship of the electrical signals received at the electrodes.

By rotating the catheter and/or moving it longitudinally and recording electrical signals, a series of maps or pictures can be produced. A series of such pictures provides a "moving" picture of successive heartbeats, which may be able to better define the ectopic sites of activation or other activation pathways that contribute to the malfunction. This type of information may then allow the cardiologist to intervene with another catheter to destroy that causative tissue. Such destruction of heart tissue is referred to as "ablation," which is a rapidly growing field within electrophysiology and obviates the need for maximally invasive open heart surgery.

In Chilson et al. the arms are easily moved relative to each other and hence, the shape of the elliptical envelope varies from time to time and may vary even when positioned in one place due to the pumping heart chamber or the effect of rotation. Accordingly, the spatial relationship of the electrodes is subject to variation of unknown amounts. This, in turn, imparts a high degree of uncertainty or error in any map of electrical activity produced with the use of this catheter.

To obtain additional improvements in mapping, Chilson et al and U.S. Pat. Nos. 5,156,151 and 5,324,284 both to Imran, which are incorporated herein by reference, utilize an internal puller wire to expand and stabilize the three-dimensional shape. The puller wires of Chilson et al. and the Imran references extend through catheter lumens which are not sealed against the flow of blood at either the proximal or distal ends of the catheters, and the puller wires of Chilson et al. and Imran are not coated. Thus, the puller wire is in direct contact with the lead wires and/or the catheter wall. Because the Chilson et al. and Imran puller wire is in direct contact with the lead wires and/or the catheter wall, which are fixed relative to the puller wire, the puller wire can become impinged between the lead wires when the catheter is bent preventing translation of the puller wire through the lumen. Further, when the puller wire is in direct contact with the lead wires, the puller wire can wear off the insulation of the lead wires or even severe the lead wires thereby destroying the catheter. Because the distal end of the catheter is not sealed against the flow of blood or air, blood can infiltrate the lumens of the catheter thereby preventing effective cleaning and sterilization of the catheter for reuse, and air can be introduced through the catheter into a blood vessel or the heart creating a potentially fatal air embolism.

SUMMARY OF THE INVENTION

The present invention provides an electrophysiological mapping catheter comprising an outer catheter and an inner catheter. The inner catheter comprises a tubular shaft extending longitudinally through the outer catheter tube. At the distal end of the shaft, there is a plurality of flexible arms, each arm carrying a plurality of spaced-apart electrodes. The flexible arms of the basket are fixed at their proximal ends to a proximal fitting and fixed at their distal ends to a distal fitting. The shaft is movable longitudinally within the outer catheter and the arms and electrodes can be retracted into and extended from the outer catheter tube. When the arms are extended out of the catheter tube, the arms flex outwardly to form a "basket," the electrodes forming a three-dimensional array.

Each arm comprises a reinforcing spine surrounded by a tubular flexible sheath having a generally circular cross-section. Each reinforcing spine preferably has a semicircular cross-section with the flat surface of the spine facing inwardly, i.e. toward the axis of the catheter. The spines preferably lie in the outwardly facing portion of the tubular sheath with the remainder of the tubular sheath filled by insulated electrode lead wires.

The electrodes are preferably formed on the arms by passing insulated lead wires through the wall of the tubular sheath, wrapping the wires around the tubular sheath and gluing it thereto. The insulation is then stripped off the outer surfaces of the lead wires which are wrapped around the sheath. The electrode lead wires extend from the arms through the proximal fitting and through the lumen of the inner catheter shaft to a stimulation and/or recording device.

The proximal and distal fittings include polygonal rod segments whose flat sides correspond in number to the number of spines and engage the flat surfaces of the spines. A clamping ring is positioned around the spines to hold them in proper orientation on the polygonal rod segment. In a preferred embodiment, the spines are formed out of a superelastic material, particularly a nickel-titanium alloy, with "shape memory." Such material returns to its bowed shape upon extension of the arms out of the outer catheter.

Also provided is a tubular catheter shaft with a plurality of arms forming a three-dimensional shape at the distal end of the catheter shaft. Each arm has at least one electrode with an electrode lead wire connected thereto. A puller wire extends through a lumen of the catheter and is attached to the distal end of the basket shape such that the basket shape can be expanded by a proximally directed force applied to the puller wire. The lumen of the catheter shaft is closed at the distal end. In another embodiment of the invention, the puller wire is coated.

Further provided is an electrode configuration having a plurality of continuous electrode arms forming a three-dimensional shape. Preferably, portions of the electrode arms are coated.

Still further provided is a method of coating the electrode arms in which a coating material is dissolved in a solvent to form a solution. The solution is applied to the electrode arm and cured thereon.

BRIEF DESCRIPTION OF THE DRAWINGS

FIG. 1 is an enlarged view of the distal end of an inner catheter and an outer catheter with the inner catheter extended from the outer catheter, thus forming a basket of electrodes at the distal end of the inner catheter;

FIG. 2 is an enlarged view of an electrode pair from the circled portion labeled "2" in FIG. 1;

FIG. 3 is a longitudinal cross-sectional view of the distal end of the inner catheter shaft;

FIG. 13 is an elevational view of an alternate electrode configuration;

FIG. 14 is an elevational view of another alternate electrode configuration;

FIG. 15 is an elevational view of still another alternate electrode configuration;

FIG. 16 is an elevational view of a further alternate electrode configuration;

FIG. 17 is a cross-sectional view taken along line 17—17 of the electrode in FIG. 16;

FIG. 18a is an elevational view of the electrode configuration of FIG. 16 having the proximal ends of the electrodes completely coated;

FIG. 18b is a cross-sectional view taken along line 18b—18b of the electrode in FIG. 18a;

FIG. 19a is an elevational view of the electrode configuration of FIG. 16 having the distal ends of the electrodes completely coated;

FIG. 19b is a cross-sectional view taken along line 19b—19b of the electrode in FIG. 19a; and FIG. 19c is a cross-sectional view taken along line 19c—19c of the catheter in FIG. 19a.

DETAILED DESCRIPTION OF THE PREFERRED EMBODIMENT

Figure 8:
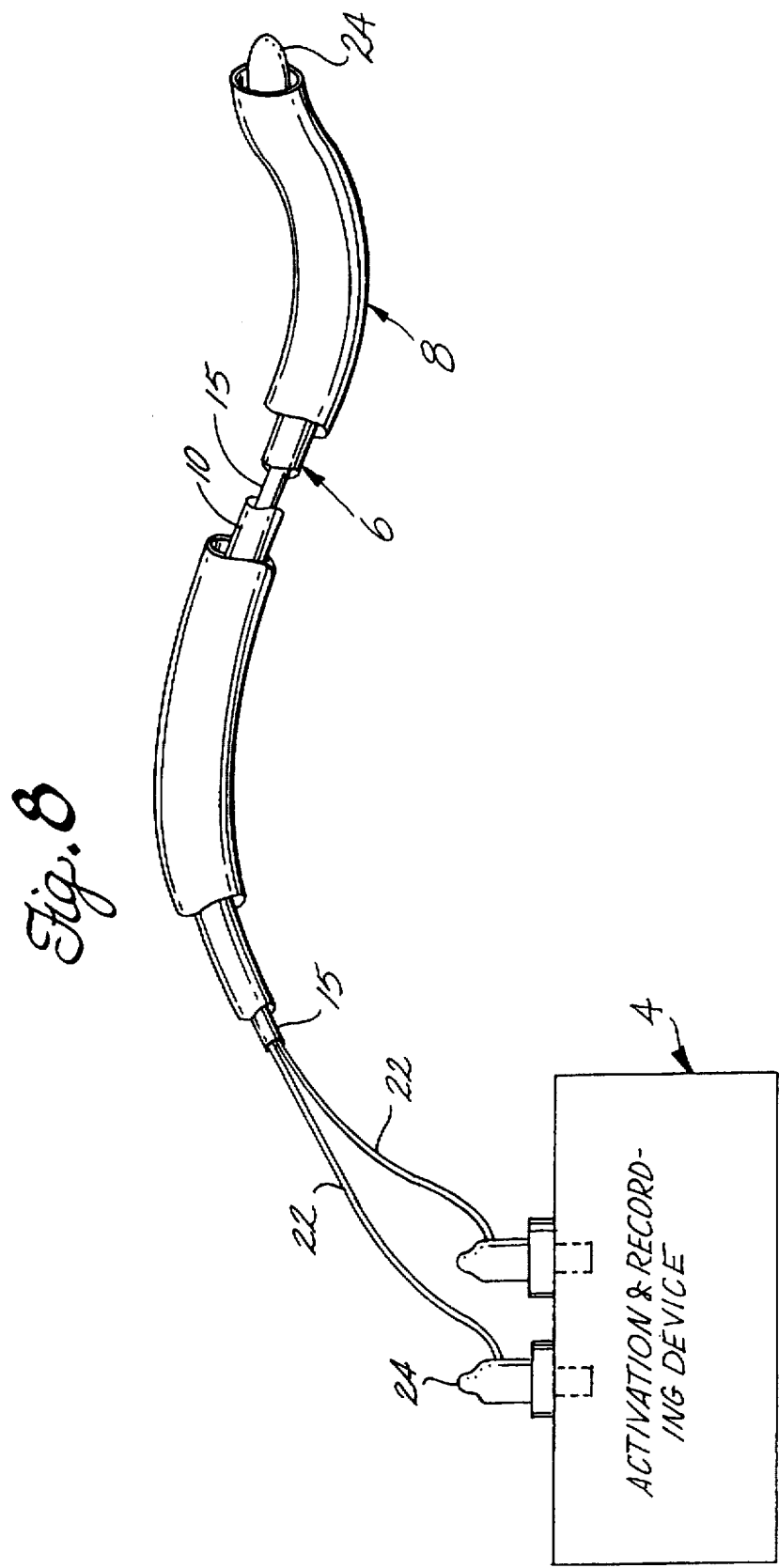
FIG. 8 is a partial perspective and partial schematic view of an electrophysiological mapping system according to the invention, including an inner catheter, an outer catheter, and an activation and recording device, showing the inner catheter retracted within the outer catheter.

With reference to FIGS. 1, 2, and 8 a preferred electrophysiological mapping system is shown. The system includes an electronic stimulation and/or recording device, an inner catheter 6, and an outer catheter tube 8. Outer catheter tube 8 carries inner catheter 6 to a mapping site, e.g., within a heart chamber, and also serves to withdraw the inner catheter 6 from the mapping site. Inner catheter 6 is slidable longitudinally within outer catheter tube 8. FIG. 8 shows the mapping system, including electronic stimulation and/or recording device 4, and inner catheter 6 retracted within outer catheter tube 8.

Inner catheter 6 comprises an elongated, tubular catheter shaft 7 and five electrode carrying arms 9 at the distal end of the catheter shaft 7. Inner catheter 6 can be moved relative to outer catheter tube 8 between an extended position as shown in FIG. 1 wherein arms 9 extend completely out of the distal end of outer catheter tube 8 and a retracted position generally as shown in FIG. 8 wherein the arms 9 are retracted within the outer catheter tube 8. In the extended position, the arms 9 bow outwardly to define a "basket" structure.

Each arm 9 has its own spaced set of ten electrodes 11, shown herein as five bipolar electrode pairs. In the embodiment shown, the five electrode pairs are generally evenly spaced. It is understood, however, that the number and spacing of the electrodes may vary as desired. Further, single electrodes may be used rather than bipolar electrode pairs.

The arms 9 are fixed at their proximal ends to a proximal fitting, generally designated 12, and also fixed at their distal ends to a distal fitting, general designated 14. Proximal fitting 12 is, in turn, fixed to the distal end of the catheter shaft 7. The catheter shaft 7 comprises a central lumen 13 which extends from its proximal end to its distal end. The shaft 7 preferably comprises a tubular wall 10 of high-strength braided stainless steel or other high-strength wire or fiber, sandwiched between inner and outer layers of firm, yet flexible, polyurethane, for example, as disclosed in U.S. patent application Ser. No. 07/645,230, filed Jan. 24, 1991, incorporated by reference herein. This high-torque shaft structure allows a physician to control the orientation of the electrode basket within the heart chamber by rotating the catheter shaft 7 where it enters the patient's body, which is usually at the groin or neck. The shaft 7 preferably further comprises a nylon stiffening sleeve 15 lining the interior of the tubular wall 10.

Figure 4:
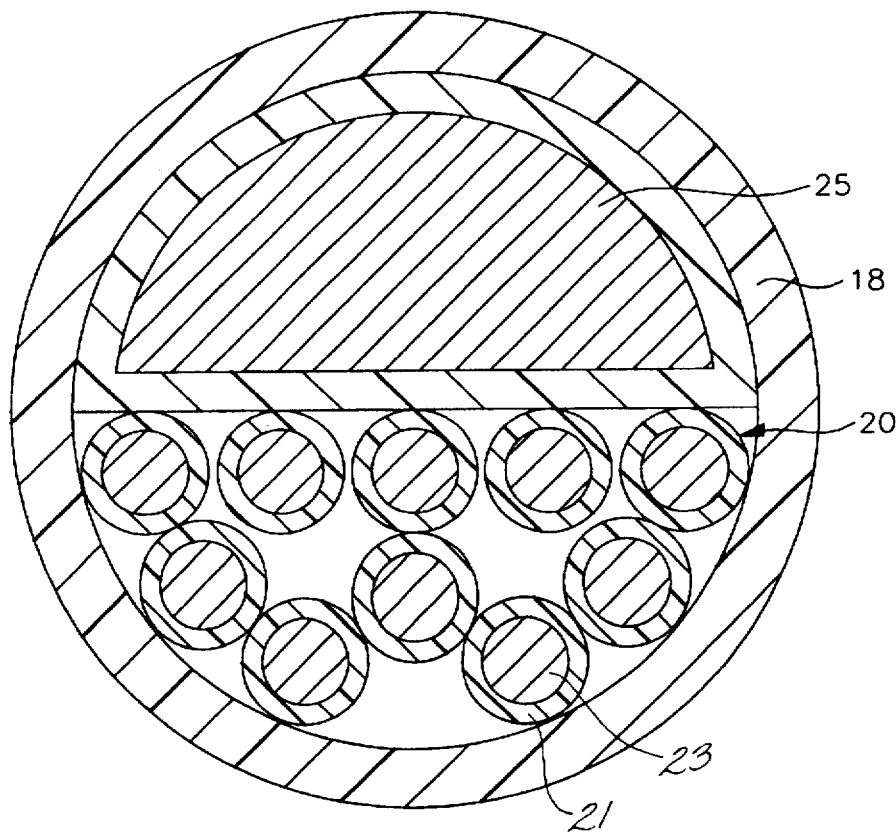
FIG. 4 is an enlarged transverse sectional view taken along line 4—4 of FIG. 1 and showing one arm of the basket of FIG. 1.

FIG. 4 is a sectional view of an arm 9. The arm 9 has an outer tube/sheath 18 of a flexible insulating material, e.g., a plastic such as flexible polyurethane tubing. Inside the plastic tubing are the plurality of electrode lead wires 20, each wire having an insulation coating 21 and a central conductive wire core 23. The wires 20 extend from the electrodes 11 through the plastic tubing 18 of the arms 9, through the proximal fitting 12 and lumen 13 of the shaft 7 to the stimulation and/or recording device 4. In this embodiment, there are fifty lead wires 20 which correspond to the ten electrodes 11 carried on each of the five arms 9. The number of electrodes and, hence, electrode lead wires may be varied as needed.

Referring to FIG. 3, the lead wires 20 are separated into five bundles 22, each bundle 22 containing the ten lead wires 20 which correspond to the ten electrodes 11 carried by each particular arm 9. At their proximal ends, the separate wire bundles 22 terminate in separate plug connectors 24, which are plugged into the activation and recording device 4 (FIG. 8). The total number of lead wires 20 in each bundle 22 is equal to the number electrodes 11 on each corresponding arm. Therefore, if there are 5 electrodes on each arm, there will be 5 leads in the corresponding bundle. If there are 5 electrode pairs, there will be 10 electrode leads in the bundle. Each bundle 22 of leads is contained in an insulated flexible tube, which in turn enters the plug connector.

With reference to FIG. 2, each electrode 11 is formed by passing a lead wire 20 through the outer sheath 18 of the arm 9. The wire 20 is wrapped tightly around the sheath 18 and glued and then the insulation coating from the outwardly facing surfaces of the lead wires, i.e. the surfaces which will contact the heart wall, is stripped to expose the metal of the lead wire.

It is preferable that the electrode lead wires 20 be of a metal which is inert in blood. MONEL 400, which is a trademark of Huntington Alloy Products Division of International Nickel Co., Inc., Huntington, W. Va., is presently preferred. MONEL refers to a group of corrosion-resistant alloys of predominantly nickel and copper and very small percentages of carbon, manganese, iron, sulfur, and silicon. Some such alloys also contain a small percentage of aluminum, titanium, and cobalt. MONEL 400 has the additional benefit that it is not as easily visible under fluoroscopic x-ray as platinum. Therefore, the electrodes can be small and all of equal size and uniformly arranged.

With materials which are more radiopaque, even spacing of the electrode is not desirable because it is difficult to distinguish which arm is at which location. For example, in U.S. Pat. No. 4,699,147 to Chilson et al., the electrodes on one arm are spaced unevenly with respect to the electrodes on each other arm. If the electrodes were spaced evenly in the device of Chilson et al., it would be difficult to identify which arm is which under x-ray. In the preferred embodiment of the present invention, the electrode pairs on each arm are able to be spaced evenly with respect to each other and are located on corresponding positions to the electrodes on each other arm, although uneven spacing on each arm and staggered spacing with respect to the electrodes on other arms is acceptable.

The even spacing of electrodes would normally result in difficulty determining which arm is at which location. However, in accordance with one aspect of the invention, markers 38, at different locations along each arm, such as in a staggered or spiral pattern, are positioned on the arms, respectively. These markers preferably are of a material which is easily identifiable under fluoroscopic x-ray, such as platinum, and are in the shape of a band or ring fixed around each arm.

The arms 9 are supported by a flexible rib or spine 25 having a semicircular cross-section which runs through the outer tube 18 as shown in FIG. 4. The spine 25 is preferably formed out of a superelastic material, such as a nickel-titanium alloy having about 54 to 57% nickel, preferably 55%, and the remainder is titanium, preferably 45%. Such materials exhibit "shape memory." That is, it can be deformed by an external stress, e.g. bent, and, when that stress is removed, it will return to its original shape. A presently preferred material is sold under the trademark NITINOL by U.S. NITINOL of Saratoga, Calif. Such a superelastic spine 25 allows the arms 9 of the basket to be retracted into and extended from the outer catheter tube 8 and otherwise subjected to bending, such as from the beating heart chamber, yet still return to its proper shape, even if extremely deformed.

The spine 25 preferably has an insulation coating 33, e.g., of polyurethane paint, to help hold it in place and shield it from the lead wires. The lead wires 20 and spine 25 are positioned in sheath 18 such that the spine 25 occupies the outwardly facing portion of the sheath 18, while the lead wires 20 occupy the inwardly facing portion of the sheath 18. The terms "outwardly" and "inwardly" are relative to an axis or centerline of the basket. Spines 25 having a semicircular cross-section are preferred over spines having circular cross-sections of the same cross-sectional area because they provide greater lateral stability, yet have sufficient flexibility for opening into the "basket" shape when the inner catheter 6 is extended out of and collapsed into outer catheter tube 8.

The positioning of the electrode lead wires 20 in the inward portion of the tube 18 places the wires 20 away from the heart wall. This enables the wire portion used for the electrodes 11 to pass through the sheath 18 at a location remote from the heart wall and thereby provide a smoother electrode surface. The hole in the sheath 18 through which the lead wire 20 extends and lead wire terminus is preferably covered and secured with an adhesive, e.g., polyurethane, in a position where it will not be in contact with the heart chamber wall.

The metal portion of each spine 25 extends beyond the plastic tubing 18 at each end and attaches to the two fittings 12 and 14, as shown in detail in FIGS. 3–6. The proximal fitting 12 is formed by a polygonal rod segment 26 having an axial aperture 32 formed therein. The rod segment 26 is preferably metal. The number of sides of the polygonal rod segment 26 equal the number of spines 25. The flat surface of each spine 25 is positioned flat against the side of the polygonal rod segment 26 in the same orientation as the spines 25 are located in forming the basket.

An outer clamping ring 27, e.g., of metal, holds the spines 25 in place against the sides of the polygonal rod segment 26. An adhesive, such as polyurethane or epoxy, is preferably used to permanently fix the spines, polygonal rod segment 26, and clamping ring.

The proximal fitting 12 is fixedly mounted within the distal end of the inner catheter shaft 7, e.g., by epoxy, polyurethane or other adhesives. The distal end of the nylon sleeve 15 extends up to and butts against the proximal end of the polygonal rod segment 26 and clamping ring 27. The electrode lead wires 20 from each arm 9 pass through the axial aperture 32 in the polygonal rod segment 26 and then through the nylon sleeve 15.

Distal fitting 14 is generally the same as proximal fitting 12, in that it has a polygonal rod segment 29. The spines 25 are fixed to each side, respectively, of the polygonal rod segment 29 and are secured thereto by an outer clamping ring 30. However, no aperture is needed in segment 29 because no lead wires are present at the distal fitting. In addition, it is preferable to provide an outer plastic tip member 31, which is rounded in shape at its distal end, to help the inner catheter slide through arteries or veins with minimum trauma and to prevent trauma in the heart chamber. The tip member 31 may be fixed by using adhesive, e.g., epoxy or polyurethane.

The distal fitting 14 is the same size as or, if desired, may be of a smaller scale than proximal fitting 12. These fittings 12 and 14 hold the spines 25 in proper angular orientation with respect to each other, and thus maintain the proper spacing of the arms 9 and the proper orientation of the basket. This is important because the cardiovascular catheter is subjected to a pumping heart wall and must also be rotated during the electrophysiological mapping process. In addition, the spines 25 are subjected to bending and other forces during retraction into the outer catheter and extension therefrom.

Figure 7:
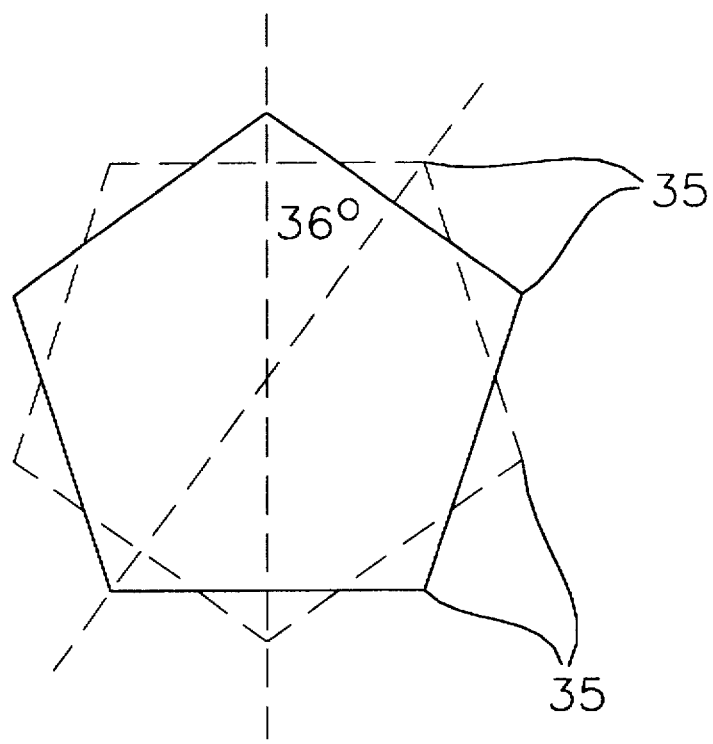
FIG. 7 is a schematic view of the ten asymmetric positions of rotation.

The basket is shown with five arms 9, which is the most preferable number. As shown in FIG. 7, there are at least ten useful asymmetrical positions of rotation. That is, the arms are placed at a first position in the heart chamber where readings are taken, and then the basket is rotated 36° where readings are again taken. As will be understood by those skilled in the art, there are an infinite number of orientations but only a limited amount of obtainable data is useful. By the use of five arms, the basket very nearly appears round in rotation when viewed from the end. This feature greatly facilitates placement and control within a heart chamber because the heart chambers are not round, but are irregular.

A greater number of arms is not preferred because differentiation of electrodes becomes more difficult and the inner catheter is more difficult to fit within the outer catheter. A lesser number of arms is more practical in that it is smaller and easier to differentiate the electrodes, but is not preferred because mapping becomes more cumbersome.

In use, the inner catheter 6 is disposed within the outer catheter 8 for placement in a vein or artery and then subsequently into a chamber of the heart. The outer catheter 8 holds the arms 9 of the basket internally in a collapsed position so that the entire catheter, consisting of the inner catheter 6 and the outer or guiding catheter 8, can be passed down the vein or artery into the heart chamber. Once the distal ends of the catheters have reached the desired heart chamber in the appropriate position, the outer catheter 8 is withdrawn so that the arms 9 flex into their predetermined "basket" position. The electrodes 11 contact the walls of the heart chamber in this position. Additional outward movement of the arms and pressure against the heart wall can be gained by pushing forward on the inner catheter shaft 7 causing the basket to widen outwardly. When mapping has been completed, the outer catheter can be extended back over the basket to collapse the arms, and then ultimately be withdrawn with the arms therein.

The inner mapping or basket catheter, as described above, has several advantages. For example, fixing the spines of the basket at both their distal and proximal ends provides a very laterally stable basket. This stability is important to hold the catheter in stable position within a beating heart chamber.

The fittings which hold the distal and proximal ends of the spines together the flat sides of the spines mating with the flat sides of the polygon, ensure accurate arrangement of the arms in three dimensions.

The semicircular cross-section of the spines increases the lateral stiffness in comparison with a round cross-section of equal area, thereby increasing the lateral stability of the basket.

The use of superelastic material, such as NITINOL, for the spine 25 results in a basket that can be bent, collapsed, and twisted without appreciable permanent deformation. It is thus highly resilient.

The use of five basket arms in conjunction with a high-torque catheter shaft achieves a basket which can readily be controlled and oriented within the heart chamber.

The use of the semicircular cross-section for the spine further allows the spines to fill the outwardly facing portion of the arm tubing, thus leaving the inwardly facing portion for the lead wires. Lead wires can thus extend through the tubing, and after being wrapped around the tubing can terminate at locations along the inwardly facing side of the arms away from the heart wall. Each exit hole and terminus can be covered and secured by adhesive. Only the outwardly facing portions of the lead wire which is wrapped around the tubing need be scraped bare to form the electrode.

The electrodes can thus be made quite small and are readily distinguished fluoroscopically from the platinum ring markers. The ring markers readily identify each arm of the basket, as they are arranged in a staggered or spiral form on the different arms.

The basket which is formed as described is not only laterally stiff, but is also quite resilient and can form itself readily to the contour of the heart chamber, by pushing the inner catheter forward after the basket has been exposed to the heart chamber through the withdrawal of the outer catheter. This helps ensure that all electrodes make good contact with the endocardial surface and provide strong electrical recording signals.

Figure 9:
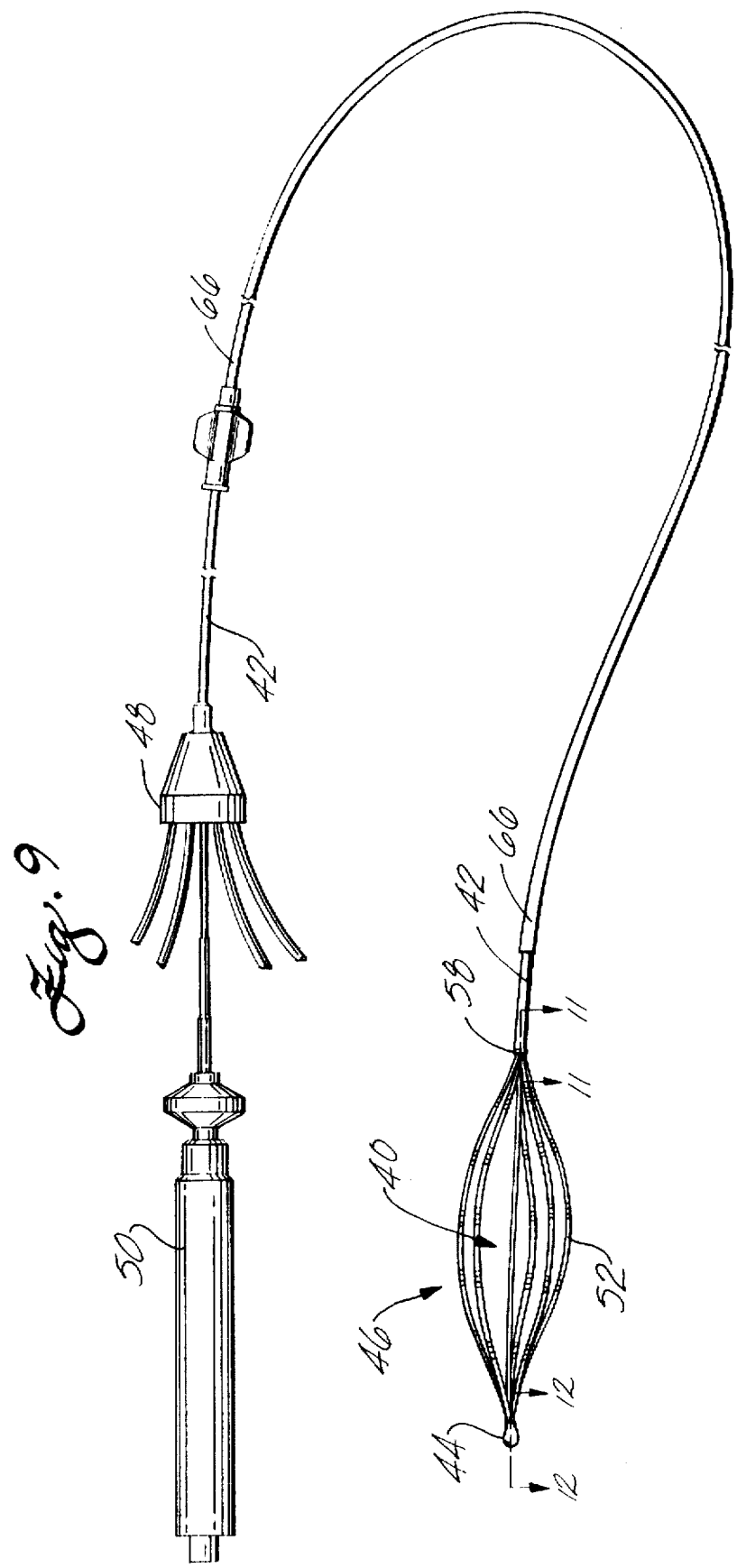
FIG. 9 is an elevational view of a catheter having a basket of electrodes in a relaxed position with a coated puller wire and a deflectable control handle for activation of the puller wire.
Figure 10:
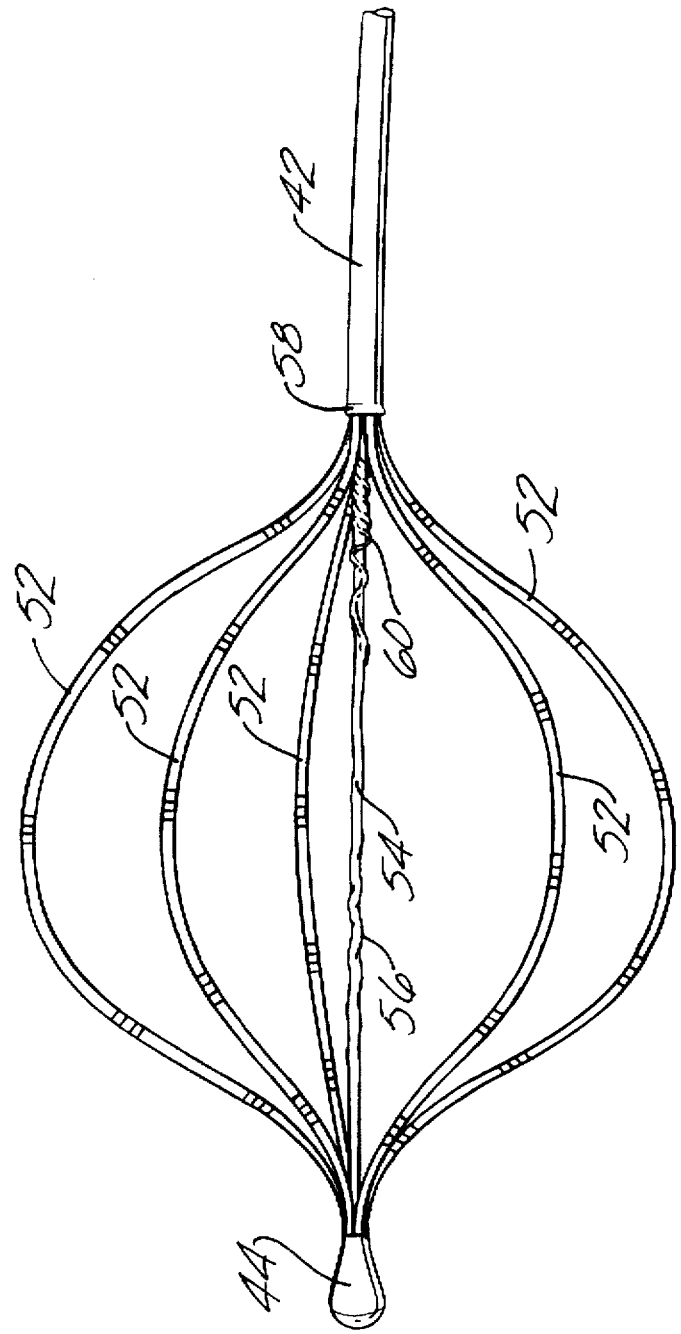
FIG. 10 is an elevational view of the basket of FIG. 9 in an expanded position.

Referring to FIG. 9, a further embodiment is shown wherein a puller wire, generally designated 40, extends through the catheter 42 and is fixed to the distal fitting 44 of the basket, generally designated 46. The puller wire extends out of the proximal end 48 of the catheter and is attached to a means for applying a proximally directed force to the puller wire. The preferred means for applying the proximal force is a deflectable control handle 50 of the type disclosed in U.S. Pat. No. 4,960,134 and U.S. Pat. No. Re. 34,502 both to Webster, Jr., which are incorporated herein by reference. When the deflectable control handle is activated, the puller wire and the distal fitting to which the puller wire is connected are pulled proximally relative to the catheter thereby expanding the basket outwardly to the position shown in FIG. 10. The outward expansion of the basket forces the arms 52 against the chamber walls thereby impeding the motion of the arms relative to each other and resisting the shifting of the basket within the heart chamber.

The external portion 54 of the puller wire is covered with a polyurethane tube 56 which is sealed at the distal fitting 44 and the proximal fitting 58 of the basket. The polyurethane tube has a diameter between 0.02 and 0.03 inch and has flares 74 and 84 (see FIGS. 11a and 12) formed on each end by stretching the tube to form a reduced diameter portion in the center of the polyurethane tube. When the polyurethane is stretched the central stretched portion becomes elastic. Because the tube is sealed at both the distal and proximal fittings, the proximal portion of the tube tends to scrunch together into an accordion-like shape 60 which in no way inhibits or interferes with the normal functions of the catheter. The polyurethane tube which is easily cleaned and sterilized prevents blood from infiltrating the puller wire and from flowing by capillary action to the internal portion of the puller wire which is infeasible to clean and sterilize. Thus, the polyurethane tube allows the catheter to be cleaned and sterilized for reuse. The internal portion 62 (see FIG. 11a and 11b) of the puller wire is coated with TEFLON® and covered with a TEFLON® sheath 64. The TEFLON coating acts as a lubricant inside of the TEFLON sheath, and the TEFLON sheath acts as a shield for the lead wires and prevents the puller wire from being impinged or pinched when the catheter is bent. Thus, the TEFLON sheath covers the puller wire preventing the puller wire from creating a large frictional force by contacting the lead wires and catheter wall. Therefore, the smooth TEFLON coated puller wire, with its low coefficient of friction, easily and smoothly slides within the TEFLON sheath relative to the lead wires and catheter walls, thereby reducing the amount of force necessary to expand the basket and allowing the puller wire to translate easily in the distal direction so that the basket is easily retracted into the outer catheter 66.

As previously stated, the puller wire is attached to the distal fitting and the polyurethane tube is sealably attached to the distal end of the sheath. The details of these connections are illustrated in FIGS. 11a, 11b and 12.

Figure 11A:
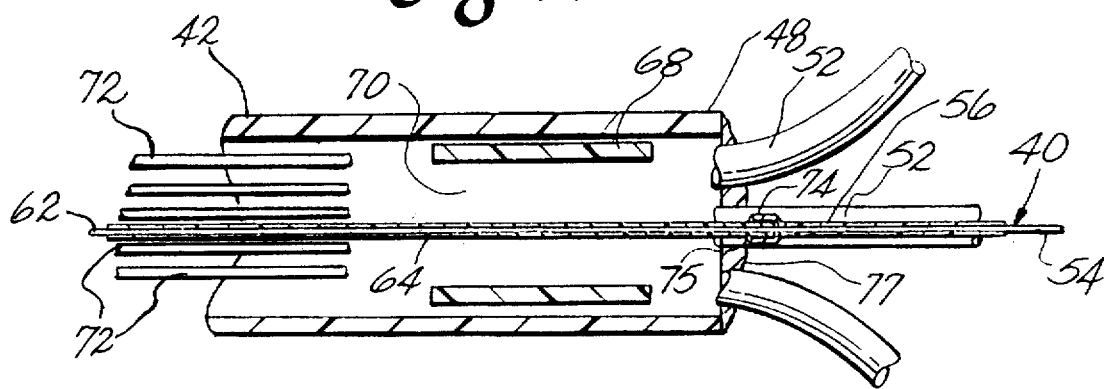
FIG. 11a is a cross-sectional view taken along line 11—11 of FIG. 9 illustrating the proximal end of the basket.

Referring to FIGS. 11a, the TEFLON sheath is sealably attached to the proximal flare 74 of the polyurethane tube 56. The polygonal rod segment 68 has an aperture 70 through which the lead wires 72 extend. The lead wires then extend into the arms 52. The portions of the arms and lead wires within the aperture and the clamping ring have been removed from FIG. 11a for clarity. The puller wire 40 and TEFLON sheath extend through the aperture 70 and out of the catheter. The polyurethane tube extends up to the proximal fitting and has a flare 74 at its proximal end. The TEFLON sheath extends into the flair of the polyurethane tube. The TEFLON sheath and the polyurethane tube form a circumferential lap joint which is welded 75 shut with polyurethane. The proximal fitting in the distal end of the catheter is sealed with a polyurethane seal 77 thereby preventing blood from entering the catheter. Thus, the catheter can be cleaned sterilized and reused. Further, the seal 77 prevents air from entering the heart, and thus, preventing potentially fatal air embolism. With the puller wire enclosed in the polyurethane tube, which is fixed to the distal end of the catheter, it is possible to seal the catheter without interfering with the function of the puller wire. That is, the puller wire can slide freely in a tube which is sealably fixed to the distal end of the catheter. Further the welded polyurethane seal 77 is not subject to failure because there is no packing through which the puller wire must pass.

Figure 11B:
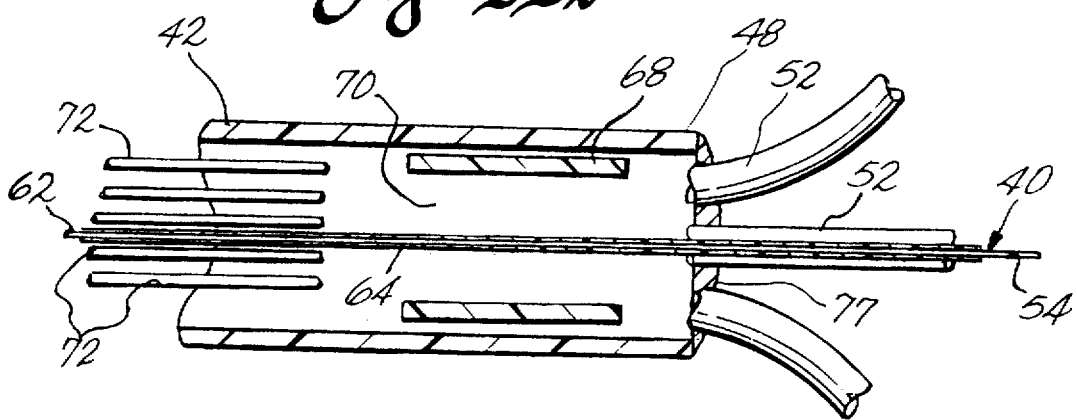
FIG. 11b is a cross-sectional view taken along line 11—11 of FIG. 9 illustrating the proximal end of the basket and an alternate embodiment of the coating on the puller wire.

FIG. 11b shows an alternate embodiment of the coated puller wire in which the TEFLON sheath extends all the way to the distal fitting of the basket and is sealably attached to the distal fitting. The polyurethane tube is preferred to the TEFLON sheath because the polyurethane tube is elastic, and hence, less of an accordion shape 60 is encountered with the use of the polyurethane tube.

Figure 12:
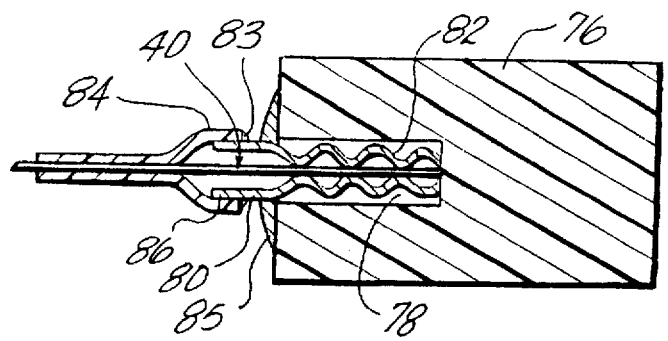
FIG. 12 is a cross-sectional view taken along line 12—12 of FIG. 9 illustrating the distal end of the basket.

Referring to FIG. 12, the distal polygonal rod segment 76 has a bore 78 into the proximal side of the fitting. The distal end of the puller wire is inserted through a crimping tube 80 which is a hollow twenty-seven (27) gauge needle. The distal end 82 of the crimping tube is then crimped onto the puller wire, and the distal end of the crimping tube is inserted into the bore of the distal polygonal rod segment and nonremovably soldered 85 therein. The polyurethane tube also has a flare 84 at its distal end which is fitted over the proximal end 86 of the crimping tube forming a lap joint between the crimping tube and the polyurethane tube. The polyurethane tube is then welded 83 to the crimping tube with polyurethane. The distal fitting is, therefore, sealed because the soldering of the crimping tube to the polygonal rod segment seals the distal end of the puller wire from the blood stream and the polyurethane tube is circumferentially welded to the crimping tube preventing blood from reaching the puller wire.

The bore is centrally located in the distal rod segment, and the aperture 70 through which the puller wire passes is so small relative to the basket that the puller wire is positioned substantially central with respect to the basket. Thus, the puller wire is coaxial with the central axis of the basket, and the outward expansion of the basket is, therefore, uniform.

In use, right heart catheterization is performed by inserting an introducer into the femoral vein. The introducer is then guided through the inferior vena cava, is and into the right atrium, and if required, it is guided into the right ventricle. The basket catheter is then pushed through the introducer into the heart. Left heart catheterization is performed by inserting an introducer into the femoral artery. The introducer is then guided through the iliac artery, the aorta, through the aortic valve and into the left ventricle. In the alternative, a right sided approach can be used entering the left atrium transeptally. The basket catheter is then pushed through the introducer into the heart. The catheterization procedure can be performed with less difficulty and with less trauma to the blood vessels by the use of steerable catheters/introducers, and catheters/introducers with soft deformable tips. U.S. Pat. No. 4,531,943 to Van Tassel et al., which is incorporated herein by reference, discloses a catheter with a soft deformable tip for reducing the trauma to the blood vessels during catheterization. U.S. Pat. No. 5,045,072 to Castillo et al., which is incorporated herein by reference, discloses a flexible tip catheter. Further the catheters/introducers may have a predisposed bend or bends which, depending upon the type of catheterization to be performed, are bent in a certain direction to simplify that specific type of catheterization.

In FIGS. 13 through 16 alternate electrode configurations are illustrated which can be used for different types of ablation and mapping. After the required mapping has been performed and problematic areas are located, radio frequency can be provided to the electrodes of the existing catheter for ablation or if a specialized type of ablation is needed, the catheter may be removed and a catheter having an electrode arrangement such as that in FIG. 13 can be inserted into the introducer, properly oriented in the heart, and used to ablate the problematic tissue.

The electrode configuration of FIG. 13 provides a wide electrode array with a spiral pattern. The arms 88 have closely spaced electrodes 90 so that detailed mapping is obtained. The electrodes spiral down the arms 88 starting with arm 88A having electrodes in the most distal position then to arm 88B with the electrodes being slightly proximal of the electrodes on arm 88A. The electrodes on arm 88C are then slightly proximal of the electrodes on arm 88B, and the electrodes on arm 88D are just proximal of the electrodes on arm 88C. Finally, the electrodes on arm 88E are located just proximal of the electrodes on arm 88D, and thus, the arm 88E electrodes 0are the most proximal electrodes. An angle α is defined by a line 87 which is perpendicular to the axis of the catheter and a line 89 which is defined by the two most proximal electrodes on any two adjacent arms, except the A and E arms, and the angle α of the spiral can be adjusted to meet the specific mapping requirements. Thus, the electrodes can form a circle or a spiral which spans the entire length of the basket. This type of electrode configuration is especially useful for mapping atrial rhythms.

FIG. 14 illustrates an electrode configuration in which three rings 92A, 92B, and 92C of bipolar electrodes are placed around the arms 94 of the basket. This electrode configuration is especially useful for mapping and ablation in the right atrium. With the tip inserted into the coronary sinus opening, the most distal ring of electrodes 92C is positioned around the coronary sinus opening, and because the tip is inserted into the coronary sinus opening, the proximal ring of electrodes is located next to the edge of the coronary sinus opening. Thus, the right atrium can be accurately mapped around the coronary sinus opening, and if necessary, an ablation line can be made around the entire circumference of the coronary sinus opening. This method can be used with other openings in the walls of the heart chambers by adjusting the location of the distal ring 92C of electrodes. For openings having larger diameters, the distal ring would be moved proximally. Thus, the distal ring would have, when the basket is expanded, a diameter which is slightly greater than the diameter of the target opening. For openings having smaller diameters, the distal ring would be moved distally thereby reducing the diameter of the electrode ring when the basket is expanded.

FIG. 15 shows another alternate configuration of electrodes. A bipolar electrode 98 is placed on each arm 100. The electrodes form a narrow ablation line which spirals starting with the most distal electrode on arm 100A running to the next most proximal electrode on arm 100B to the middle electrode on arm 100C to the next most proximal electrode on arm 100D and finally to the most proximal electrode on arm 100E. Therefore, a thin ablation line is made which spirals from the distal electrode on arm 100A to the proximal electrode on arm 100E. An angle β is defined by a line 101 which is perpendicular to the axis of the catheter and a line 103 which is defined by the two most proximal electrodes on any two adjacent arms except the A and E arms, and the angle β of the spiral can be varied to meet specific ablation needs. Therefore, the electrodes can form a circle or a spiral which spans the entire length of the basket. The electrodes used in the embodiments of FIGS. 13–15 can be rings of any suitable electrically conductive material, but the rings are preferably fabricated from platinum or alloys of platinum and iridium.

FIG. 16 shows an alternate electrode configuration in which each arm 102 is an electrode over its entire length. Thus, the arm is a continuous electrode. Each arm comprises a NITINOL band or other inert conductive material having a generally semicircular cross section as shown in FIG. 17. The side 104 of the NITINOL band facing inwardly, that is, away from the wall of the heart chamber, is coated with a polyurethane coating 106 or other insulating material and thus, is a non-ablating area. The polyurethane, which has high viscosity and a short pot life, can be obtained from E. V. Roberts, Culver City, Calif. by referencing the identification number RF-1737.

As shown in FIG. 17, the coating may also be applied to the edges 110 of the NITINOL band. Thus, the side 108 of the NITINOL wire facing the wall of the heart chamber is an exposed ablation area and can transmit radio frequency energy to the heart wall for ablation. This forms a long narrow ablation line along the length of the electrode. Depending on where the ablation is necessary, a different electrode arm is chosen for the ablation. Though the electrodes shown are semicircular in cross-section, other cross-sectional shapes such as circular or elliptical can be utilized. These cross-sectional shapes would have inner and outer faces corresponding to the inner and outer sides of the band.

The inward side 104 and the edges 110 are coated to prevent the radio frequency energy from creating a build up of blood on the band and to reduce the amount of radio frequency energy necessary to perform the required ablation. The maximum radio frequency energy which can be transmitted by the lead wires is limited by the heating of the lead wires. By reducing the radio frequency energy transmitted to the blood, longer ablation lines can be made because more of the maximum radio frequency energy which can be transmitted by the lead wires is used for ablation.

Further, greater or smaller portions of the electrodes can be coated. In an alternate embodiment shown in FIGS. 18a and 18b, the entire proximal half, generally designated 111, or part of the proximal end of each electrode arm is coated with a polyurethane coating 114. The distal half, generally designated 116, has coating 118 on the inner side 120 and edges 122 leaving only the outer sides 112 of the distal half of the electrode arms uninsulated and available for ablation. Alternatively, as illustrated in FIGS. 19a, 19b and 19c the entire distal half, generally designated 124, or part of the distal end of each electrode arm is coated with a polyurethane coating 126. The proximal half, generally designated 128, has coating 130 on the inner side 132 and edges 134 leaving only the outer sides 136 of the proximal half of the electrode arms uninsulated and available for ablation. Thus, it can be seen that any part of the electrodes can be coated depending on the requirements of specific ablation applications. These embodiments serve to localize the application of the radio frequency energy to the area needed thereby further reducing the amount of radio frequency energy transmitted to the blood and tissue which does not need to be ablated. Thus, the total amount of radio frequency energy needed for ablation is reduced.

Figure 5:
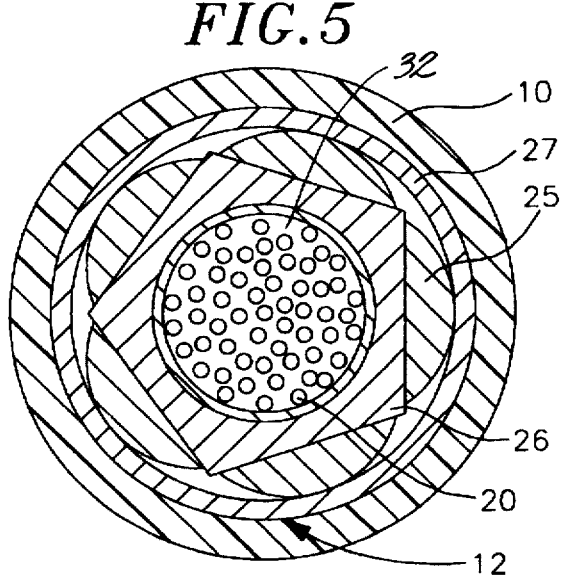
FIG. 5 is a transverse sectional view of a proximal fitting which has been taken along line 5—5 of FIG. 1.
Figure 6:
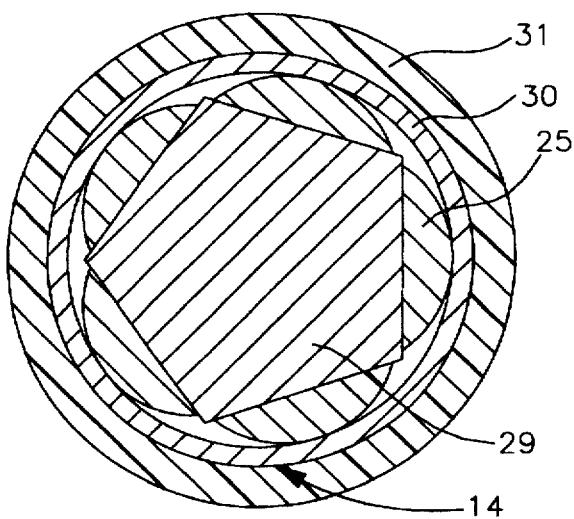
FIG. 6 is a transverse sectional view of a distal fitting of the basket of FIG. 1 taken along line 6—6 of FIG. 1.

As shown in FIG. 5, the electrode arms can be fixed to the proximal fitting 26 of the basket. The arms are then connected to the radio frequency generator with lead wires. This arrangement is preferred if a puller wire is used. However, referring to FIG. 19c the electrode arms 146 can extend through the catheter 142 and connect directly to the radio frequency generator. The electrode arms inside the catheter 142 of this embodiment have an insulating sheath 148 similar to the sheath on the lead wires and puller wire 144 extends through the catheter 142.

To apply the polyurethane coating to the NITINOL band, the polyurethane is dissolved in a solvent composed of approximately two parts tetrahydrofuran to one part p-dioxane which lowers the viscosity of the polyurethane for application to the electrode arm. Tetrahydrofuran can be obtained from Aldrich Chemical Co., Inc., Milwaukee, Wis., and p-dioxane can be obtained from E.M. Science, Gibbstown, N.J. Once the polyurethane is completely dissolved in the solution, the solution is applied to the arms of the electrode to cover the non-ablating areas of the electrode arms discussed above. The solution can be applied by painting it onto the electrode with an artist's brush, dipping the electrode, submerging the electrode, or spraying the solution onto the electrode. Alternatively, the coating can be obtained by dipping the electrode in a latex solution and completely coating it with a very thin coating of an elastomer such as a polyurethane latex with a shore hardness of 50 D or less. The latex is then fully cured by heating in a dry oven. When the electrode arm is coated by submerging or dipping, the coating is removed from the ablating areas of the electrode by sandblasting with a Comco sandblaster using sodium bicarbonate which is directed in a well defined jet at the ablating areas of the electrodes. The jet of sodium bicarbonate removes the coating with high resolution leaving the electrode undamaged.

To assure the accurate application of the solution, the portions of the electrodes which are not to be coated can be covered with a tape 138 (see FIG. 19a) thereby preventing solution from directly contacting the electrodes in those areas. The tape 138 is adhesive on one side so that it can be added to the outer surface 136 of the electrodes, and it is fabricated from a material capable of withstanding the curing temperatures of the solution. The masking process simplifies the coating of electrodes having different cross-sections such as circular and provides a method for controlling the width of the ablation line. The electrode with the solutions thereon are then heated for approximately 2 hours at approximately 100° C. or until the polyurethane has cured. Though polyurethane is preferred, other electrically insulating materials which are bio-compatible and maintain adhesion in the vascular system can be used. The tape is then removed after curing.

The invention has been described in its preferred embodiment. Numerous variations of the invention will be evident to those of ordinary skill in the art. The appended claims not only cover the preferred embodiment, but also such variations.

What is claimed is:

1. A catheter for cardiac mapping and ablation comprising:

a catheter body having a distal end and a lumen;

a plurality of arms extending through the lumen and out the distal end of the catheter body for forming a three-dimensional shape, each arm having a semi-circular transverse cross-sectional shape and wherein each arm forms a continuous electrode.

2. The catheter of claim 1 wherein each arm has a distal end and wherein the catheter further comprises a distal fitting fixing the distal ends of the arms thereto.

3. The catheter of claim 1 wherein the arms have a portion inside the catheter body which insulated.

4. A mapping and ablation catheter comprising:

a catheter body having a lumen and a distal end; and a plurality of electrically conductive electrode arms extending from the distal end of the catheter body forming a three-dimensional shape, each arm having an inward surface and an outward surface, wherein at least a portion of the inward surface is coated with a non-conductive material and wherein the outward surface has a semi-circular transverse cross-sectional contour and forms a continuous electrode.

5. A catheter basket electrode configuration for use with a catheter, the electrode configuration comprising a plurality of solid metal arms forming a three-dimensional shape, each arm having an inward surface and an outward surface, a proximal end and a distal end, and wherein the inward surface of at least one arm is at least partially coated with an insulating material.

6. The configuration of claim 5 wherein the proximal ends of the arms are fixed together and the distal ends of the arms are fixed together and the arms are expanded radially outward forming the three-dimensional shape.

7. The configuration of claim 5 wherein each arm is at least partially insulated.

* * * * *